US008922765B2

(12) United States Patent
Fujimura et al.

(10) Patent No.: US 8,922,765 B2
(45) Date of Patent: *Dec. 30, 2014

(54) CELLS FOR BIOCHEMICAL ANALYSIS, KIT FOR BIOCHEMICAL ANALYSIS, AND BIOCHEMICAL ANALYZER

(71) Applicant: Hitachi, Ltd., Tokyo (JP)

(72) Inventors: Toru Fujimura, Tokyo (JP); Kosuke Kuwabara, Tokyo (JP); Tatsuro Ide, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/961,173

(22) Filed: Aug. 7, 2013

(65) Prior Publication Data

US 2013/0315784 A1 Nov. 28, 2013

Related U.S. Application Data

(60) Continuation of application No. 13/658,872, filed on Oct. 24, 2012, now Pat. No. 8,525,985, which is a continuation of application No. 13/303,830, filed on Nov. 23, 2011, now Pat. No. 8,325,335, which is a continuation of application No. 12/923,860, filed on Oct. 12, 2010, now Pat. No. 8,089,624, which is a division of application No. 12/662,928, filed on May 12, 2010, now Pat. No. 7,834,998, which is a division of application No. 11/699,362, filed on Jan. 30, 2007, now Pat. No. 7,742,165.

(30) Foreign Application Priority Data

Mar. 7, 2006 (JP) .................................. 2006-061593

(51) Int. Cl.
*G01N 21/00* (2006.01)
*G01N 21/55* (2014.01)
*G01N 21/05* (2006.01)
*G01N 21/31* (2006.01)
*G01N 21/03* (2006.01)

(52) U.S. Cl.
CPC ................ *G01N 21/55* (2013.01); *G01N 21/05* (2013.01); *G01N 2021/0346* (2013.01); *G01N 21/31* (2013.01)
USPC .......... 356/244; 356/246; 422/82.05; 422/69; 435/287.2

(58) Field of Classification Search
CPC ....... G01N 21/55; G01N 21/05; G01N 21/31; G01N 2021/0346
USPC .......... 356/244, 246, 39–41; 422/56, 61, 100, 422/82.05, 82.09, 69; 250/573, 216, 574; 435/287.2, 288.3, 293.1, 420, 4, 6
See application file for complete search history.

(56) References Cited

U.S. PATENT DOCUMENTS 3,486,829 A 12/1969 Wilks, Jr.
4,781,456 A 11/1988 Nogami (Continued)

OTHER PUBLICATIONS

Toru Fujimura et al., "Silicon-Based Optical Thin-Film Biosensor Array for Real-Time Measurements of Biomolecular Interaction", Japanese Journal of Applied Physics, 2005, vol. 44, No. 4B, pp. 2849-2853.

(Continued)

*Primary Examiner* — Sang Nguyen
(74) *Attorney, Agent, or Firm* — Stephen J. Weyer, Esq.; Stites & Harbison, PLLC

(57) ABSTRACT

The invention makes it possible to measure binding of a biochemical substance with a high throughput and with high sensitivity using a small cell capable of being filled with a small amount of chemical solution. A space between a first substrate and a second substrate such that probes are immobilized on their mutually facing planes is used as a cell that houses a specimen solution. Light is irradiated from a first substrate side, and reflected light is subjected to spectroscopy. Binding of the target with the probe is detected by a wavelength shift in the refection spectrum.

4 Claims, 20 Drawing Sheets

(56) References Cited

U.S. PATENT DOCUMENTS

| | | | |
|---|---|---|---|
| 4,980,551 A * | 12/1990 | Wong | 250/338.1 |
| 5,362,445 A | 11/1994 | Miyahara et al. | |
| 5,418,136 A * | 5/1995 | Miller et al. | 435/5 |
| 5,468,606 A * | 11/1995 | Bogart et al. | 435/5 |
| 5,677,196 A | 10/1997 | Herron et al. | |
| 5,747,349 A | 5/1998 | van den Engh et al. | |
| 5,814,565 A | 9/1998 | Reichert et al. | |
| 5,959,728 A | 9/1999 | Nishimoto et al. | |
| 6,017,434 A | 1/2000 | Simpson et al. | |
| 6,078,705 A | 6/2000 | Neuschager et al. | |
| 6,188,474 B1 | 2/2001 | Dussault et al. | |
| 6,198,530 B1 * | 3/2001 | Leyderman | 356/244 |
| 6,376,231 B1 | 4/2002 | Enomoto et al. | |
| 6,432,364 B1 * | 8/2002 | Negami et al. | 422/82.11 |
| 6,438,279 B1 * | 8/2002 | Craighead et al. | 385/12 |
| 6,457,361 B1 | 10/2002 | Takeuchi et al. | |
| 6,485,905 B2 | 11/2002 | Hefti | |
| 6,498,353 B2 | 12/2002 | Nagle et al. | |
| 6,600,558 B2 | 7/2003 | Ueno et al. | |
| 6,716,629 B2 | 4/2004 | Hess et al. | |
| 6,818,395 B1 * | 11/2004 | Quake et al. | 435/6.1 |
| 7,023,544 B2 * | 4/2006 | Cunningham et al. | 356/326 |
| 7,197,196 B2 * | 3/2007 | Lin et al. | 385/12 |
| 7,269,308 B2 | 9/2007 | Tono et al. | |
| 7,306,941 B2 | 12/2007 | Fujimura et al. | |
| 7,439,073 B2 * | 10/2008 | Fujimura et al. | 436/164 |
| 7,569,354 B2 | 8/2009 | Okano et al. | |
| 7,619,235 B2 * | 11/2009 | Gunning et al. | 250/573 |
| 2002/0176804 A1 | 11/2002 | Strand et al. | |
| 2003/0162283 A1 | 8/2003 | Kuno et al. | |
| 2004/0101870 A1 | 5/2004 | Caubet et al. | |
| 2005/0014246 A1 | 1/2005 | Kohara et al. | |
| 2005/0227374 A1 * | 10/2005 | Cunningham | 436/518 |
| 2006/0238681 A1 * | 10/2006 | Murakami et al. | 349/117 |
| 2006/0246573 A1 | 11/2006 | Kurane et al. | |

OTHER PUBLICATIONS

Torbjorn Sandstrom et al., "Visual Detection of Organic Monomolecular Films by Interference Colors", Applied Optics, vol. 24, No. 4, Feb. 1985, pp. 472-479.

M. Harris et al., "The Relationship Between Optical Inhomogeneity and Film Structure", Thin Solid Films, vol. 57 (1979), pp. 173-178.

* cited by examiner

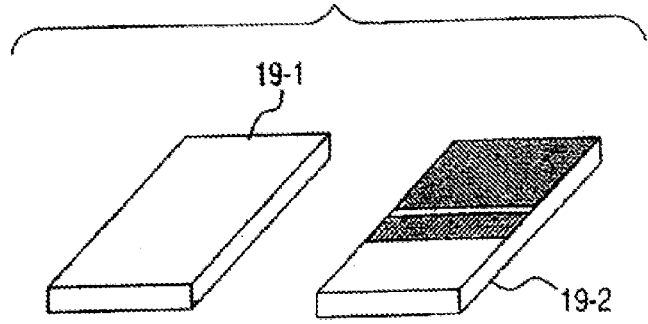
FIG. 19A
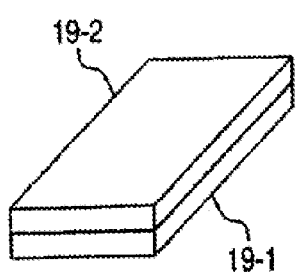
FIG. 19B
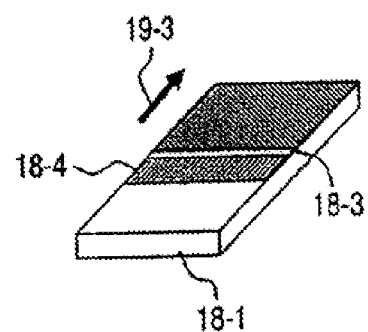
FIG. 19C
FIG. 19D
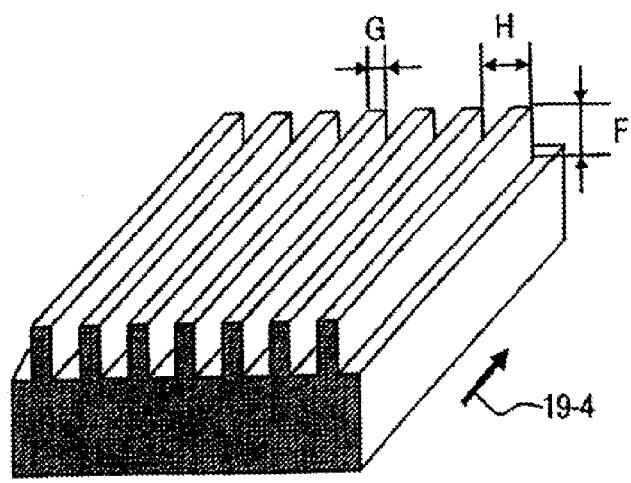

CELLS FOR BIOCHEMICAL ANALYSIS, KIT FOR BIOCHEMICAL ANALYSIS, AND BIOCHEMICAL ANALYZER

CROSS-REFERENCE TO RELATED APPLICATIONS

This application is a Continuation of U.S. application Ser. No. 13/658,872 filed Oct. 24, 2012, which is a Continuation of U.S. application Ser. No. 13/303,830 filed Nov. 23, 2011, which is a Continuation of U.S. application Ser. No. 12/923,860 filed Oct. 12, 2010, which is a Divisional of U.S. application Ser. No. 12/662,928 filed May 12, 2010, which is a Divisional of U.S. application Ser. No. 11/699,362 filed Jan. 30, 2007. Priority is claimed based on U.S. application Ser. No. 13/658,872 filed Oct. 24, 2012, which claims the priority of U.S. application Ser. No. 13/303,830 filed Nov. 23, 2011, which claims the priority date of U.S. application Ser. No. 12/923,860 filed Oct. 12, 2010, which claims the priority date of U.S. application Ser. No. 12/662,928 filed May 12, 2010, which claims the priority date of U.S. application Ser. No. 11/699,362 filed Jan. 30, 2007, which claims the priority date of Japanese Patent Application No. 2006-061593 filed Mar. 7, 2006, all of which is incorporated by reference.

FIELD OF THE INVENTION

The present invention relates to cells for biochemical analysis, a kit for biochemical analysis used for detection of a biochemical substance, and a biochemical analyzer.

BACKGROUND OF THE INVENTION

Conventionally, measurement of binding between biochemical substances, such as an antigen-antibody reaction, has been generally performed by using labels, such as radioactive substances and fluorescent substances. The use of labels needs time. Especially, in using them in a protein, there are a case where the method is complicated and a case where properties of a protein will change.

To circumvent these problems, a biochemical sensor that uses a change of interference color of an optical thin film is known as a method of directly measuring the binding between biochemical substances without using a label. A paper by T. Sandstrom, et al., Applied Optics, 1985, 24, 472-479 (nonpatent document 1) describes this biochemical sensor. Its example will be explained using a model of FIG. 1. An optical thin film 1-2 is formed on a substrate 1-1. The refractive index of air is 1.00, and the optical thin film 1-2 is a material of a refractive index of 1.50. The substrate having a refractive index of 2.25 is used. If an optical thickness of the optical thin film is chosen to be ¼ of a visible light wavelength $\lambda_0$ or one of its odd multiples (¾$\lambda_0$, ⁵⁄₄$\lambda_0$, etc.), the optical thin film acts as an antireflective film, producing an interference color. On this optical thin film 1-2, a monomolecular layer of a first biochemical substance 1-3 is formed. If the biochemical substance is considered a protein, its refractive index is of the order of 1.5 and its layer thickness is of the order of 10 nm. At this time, as shown by a reflection spectrum A of FIG. 2, the intensity of reflected light in a direction perpendicular to the optical thin film becomes zero at wavelength $\lambda_0$. When a second biochemical substance 1-4 forms bond with this first biochemical substance 1-3 biochemically, a change in the reflection spectrum from a solid line A of FIG. 2 to a dashed line A' occurs, causing the interference color to change. By this change, binding of the second biochemical substance is detected. As a general procedure of detection, first, the optical thin film 1-2 on the substrate 1-1 covered with the monomolecular layer 1-3 of the first biochemical substance is prepared. This is immersed in a solution of the second biochemical substance. Subsequently, it is taken out from the solution and dried, a change of the interference color from the solid line A of FIG. 2 to the dashed line A' is examined. Moreover, the document describes that the use of a material that is an optical absorbing material, for example, silicon, as a material of the substrate 1-1 can suppress an effect on the measurement caused by the optical reflection generated by the back of the substrate. As in the above, the nonpatent document 1 describes a technique wherein, after the sensor is taken out into air and dried, the interference color is measured.

On the other hand, if a material of a refractive index of approximately 2.2 is used as the optical thin film, a clear interference color can be obtained in an aqueous solution, and accordingly the amount of binding of the first biochemical substance and the second biochemical substance can be measured in real time in the aqueous solution (see a paper by T. Fujimura, et al., Jpn. J. Appl. Phys. 2005, 44, 2849-2853; nonpatent document 2). Its example will be explained using a model of FIG. 3. An optical thin film 3-2 is formed on a silicon substrate 3-1. The optical thin film 3-2 is a material of a refractive index of 2.2 and its thickness is specified to be 70 nm. On this optical thin film 3-2, a monomolecular layer 3-3 of the first biochemical substance is formed. White light is made incident on that structure through an optical window 3-4 made of a transparent material, and a reflection spectrum of the sensor is measured. Moreover, if a bundle of optical fiber is used as a light guide for irradiating white light and collecting reflected light, the size of the sensor can be designed to be of a diameter of submillimeter. FIG. 4 shows the reflection spectrum. In calculation of the reflection spectrum shown in this FIG. 4, since reflection of the light on the surface of the optical window 3-4 hardly affects the measurement, it is ignored. This is done because, by setting a separation between the optical window 3-4 and the optical thin film 3-2 to, for example, approximately 0.15 mm, optical interference between the optical window 3-4 and the optical thin film 3-2 can be prevented from affecting the measurement. The refractive index of a material between the optical window 3-4 and the optical thin film 3-2 was set to a refractive index of water, i.e., 1.333. A layer 3-8 of the first biochemical substance and a layer 3-5 of the second biochemical substance are both specified to be a layer of a refractive index 1.5 and a thickness of 10 nm. A solid line B of FIG. 4 shows a reflection spectrum in the case of absence of the second biochemical substance layer 3-5; a dashed line B' of FIG. 4 shows a reflection spectrum in the case of presence of the second biochemical substance layer 3-5. If the second biochemical substance forms bond with the first biochemical substance, a change from the solid line B to the dashed line B' will occur and a minimum position of the reflectance will move to a longer wavelength side by 13.5 nm. By measuring this change, the binding of the second biochemical substance with the first biochemical substance can be measured. Here, in the nonpatent document 1, the refractive index of the layer of a biochemical substance is set to 1.5, and it can be estimated that the layer of a biochemical substance material 3 nm thick within a dimensional range of 10 μm×10 μm contains an organic material of 0.5 pg. From the estimate of this nonpatent document 1, a change of the minimum position of the reflectance of 1 nm in the nonpatent document 2 can be approximated to the amount of the binding of the biochemical substance of about 1 ng/mm$^2$. Since, by this method, measurement of binding can be done in real time in a specimen solution, saturation of a reaction can be found without taking out the sensor from the specimen solution; therefore, it can perform measurement more correctly and more quickly than the method of the nonpatent document 1.

SUMMARY OF THE INVENTION

Generally, specimen containing a biochemical substance is invaluable. When performing measurement, consumption of a specimen can be made small by reducing a space between a sensor surface and the optical window, namely the volume of a cell. However, when the separation between the sensor surface and the optical window is made smaller in order to reduce the volume of the cell, it becomes impossible to ignore an effect of optical interference between those surfaces facing each other. Moreover, adsorption of the biochemical substance on the optical window also poses a problem. As an example, FIG. 5 shows a model of the case where a layer 5-5 of a third biochemical substance adheres to an optical window 5-3. This model assumes the following: An optical thin film 5-2 of a thickness of 70 nm and a refractive index of 2.2 is formed on a silicon substrate 5-1, an optical window is provided above this, a separation between the optical window 5-3 and the optical thin film 5-2 is specified to be 240 nm, and a space 5-4 therebetween is filled with water (refractive index 1.333). The layer 5-5 of the third biochemical substance is specified to be a film of a refractive index of 1.5 and a thickness of 10 nm. FIG. 6 shows a reflection spectrum in this case. A solid line C represents a reflection spectrum in the case of absence of the layer 5-5 of the third biochemical substance; a dashed line C' represents a reflection spectrum in the case of presence of the layer 5-5 of the third biochemical substance. Contrary to the result of FIG. 4, FIG. 6 shows that the wavelength position giving a minimum in the reflection spectrum is shifted to a shorter wavelength side by adsorption of the biochemical substance on the optical window 5-3. Note that generally adsorption of the biochemical substance on the optical window 5-3 is nonspecific. Therefore, this nonspecific adsorption on the optical window 5-3 becomes a noise in the measurement.

The object of this invention is to solve the above-mentioned conventional technological problem and provide simple a cell for biochemical analysis, a kit for biochemical analysis, and a biochemical analyzer that makes it possible to measure the binding of a biochemical substance with a high throughput and with high sensitivity using a small amount of a chemical solution.

The cell for biochemical analysis of this invention is specified to be a cell that is a gap formed by mutually facing planes of a first substrate and a second substrate disposed close to each other, a probe being immobilized on the each of the planes and the gap housing a specimen solution. Then, light is irradiated onto the cell for biochemical analysis and a change in a spectrum of the reflected light is detected, whereby binding between the probe and the targeted biochemical material is detected. The cell for biochemical analysis may have a form of a flow cell.

The biochemical substance being referred to here means a substance that forms bond with other substance, including not only the substances provided in vivo, such as proteins, nucleic acids, lipid and saccharides, but also exogenous substances each of which forms bond with a molecule in a living body, such as a pharmaceutical substance and an endocrine disrupting chemical substance.

According to this invention, the binding of the biochemical substance that acts as a target to a probe can be detected with high sensitivity using a small consumption of the specimen.

BRIEF DESCRIPTION OF THE DRAWINGS

FIGS. 13A, 13B, and 13C are diagrams showing an example of a production method of a kit for biochemical analysis, in which FIG. 13A shows preparation of first and second substrates, FIG. 13B shows immobilization of probes on the first and second substrates, and FIG. 13C shows fixing of the substrates;

FIGS. 18A, 18B, and 18C are diagrams showing a production method of a kit for biochemical analysis in the case where a substrate is specified to be made of a resin, in which FIG. 18A shows preparation of the first and second substrates, FIG. 18B shows immobilization of probes on the first and second substrates, and FIG. 18C shows fixing of the substrates;

FIGS. 19A, 19B, 19C, and 19D are diagrams showing a production process of a kit for biochemical analysis using a nanoimprint method, in which FIG. 19A shows a raw material made from polystyrene and a metal mold made from nickel, FIG. 19B shows pressing of the raw material with the metal mold, FIG. 19C shows a substrate with a member for keeping separation between the substrates, and FIG. 19D is an enlarged view of the member for keeping the separation between the substrates;

FIGS. 20A, 20B, 20C, 20D, 20E, 20F, 20G, and 20H are diagrams showing a method for manufacturing a metal mold, in which FIG. 20A shows a master material of silicon wafer, FIG. 20B shows exposure of a photoresist, FIG. 20C shows removal of the photoresist, FIG. 20E shows a metal mold master, FIG. 20F shows the width and the period of a wall, FIG. 20G shows formation of a metal mold, and FIG. 20H shows a metal mold;

FIGS. 22A, 22B, and 22C are diagrams showing a production method of a kit for biochemical analysis that constitutes a flow cell, in which FIG. 22A shows preparation of the first and the second substrates, FIG. 22B shows provision of a mask on PDMS, and FIG. 22C shows adhesion of the first and second substrates;

FIGS. 25A and 25B are diagrams showing a manufacture procedure of a substrate having an optical thin film, in which FIG. 25A shows preparation of the second substrate, and FIG. 25B shows a sectional view of FIG. 25A; and FIGS. 26A and 26B are diagrams showing a method for use of a kit for biochemical analysis, in which FIG. 26A shows immobilization of probes on the slide glass and the second substrate, and FIG. 26B shows a schematic diagram showing one example of a detection unit of the biochemical analyzer according to this invention.

DESCRIPTION OF PREFERRED EMBODIMENTS OF THE INVENTION

Figure 7:
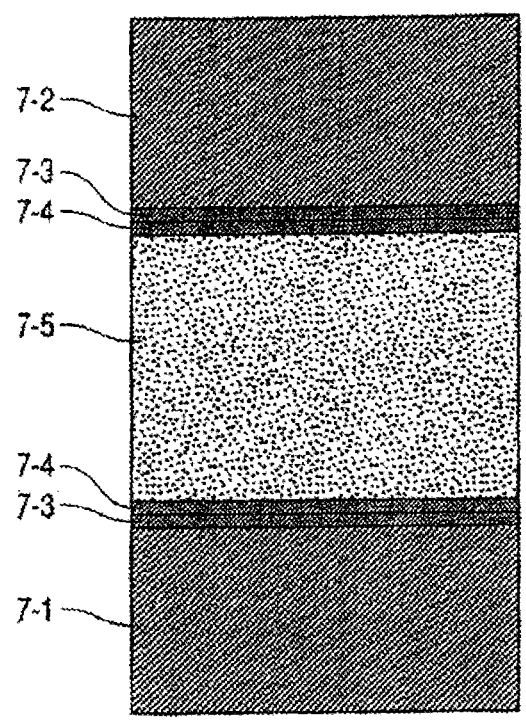
FIG. 7 is a schematic diagram showing one example of a biochemical sensor according to this invention.

Hereafter, an example of a kit for biochemical analysis and a biochemical analyzer of this invention will be described. As shown in FIG. 7, a first substrate 7-1 and a second substrate 7-2 both made up of any of glasses, polystyrene, PDMS (polydimethyl siloxane), etc. are prepared. A biochemical substance 7-3 acting as a probe (hereinafter referred to simply as a probe) is immobilized on surfaces of the first and second substrates. The surfaces on which the probe are immobilized are faced each other. A space formed between theses surfaces faced each other serves as a cell in which a solution containing a specimen is introduced. Moreover, in order to detect binding of the biochemical substance that is intended to be a target (hereinafter referred to simply as a target) with the probe, a light source and a detector are prepared. Light from the light source is irradiated from one substrate side, and light reflected from the first substrate and the second substrate is detected with a detector. In this embodiment, the light is irradiated from the first substrate 7-1 side. A specimen solution is introduced into the cell, and the binding of the target with the probe is detected from an intensity change of the reflected light at wavelengths. In order to prevent the reflected light generated at a plane opposite to a plane of the second substrate 7-2 on which the probe is immobilized from entering the detector to inhibit the measurement, one of the following measures is preferable: using an optical absorbing material as the second substrate 7-2; making a plane opposite to a plane of the second substrate 7-2 on which the probe is immobilized nonparallel thereto so that this reflected light may not immediately return to the detector; and forming an antireflective coating on a plane opposite to the plane of the second substrate 7-2 on which the probe is immobilized in order to weaken the intensity of this reflected light.

Figure 8:
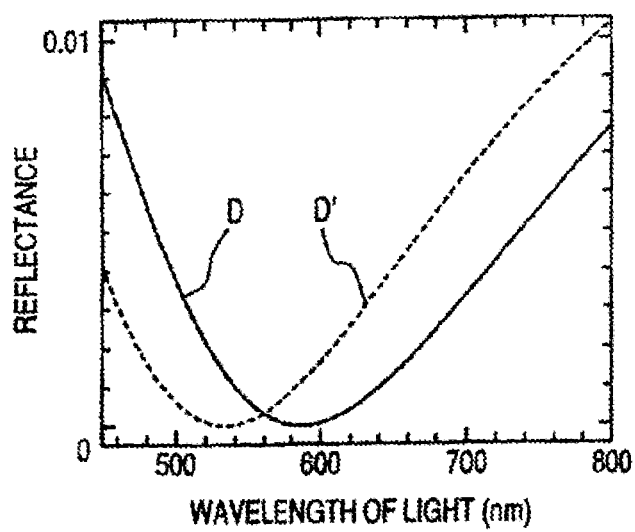
FIG. 8 is a diagram showing a calculation result of the reflection spectrum.

FIG. 8 shows a calculation result of the reflection spectra in the case where the separation between the first substrate 7-1 and the second substrate 7-2 is set to 240 nm, the layer 7-3 of the probe and a layer 7-4 of the target are both specified to be a layer having a refractive index of 1.5 and a thickness of 10 nm, respectively, and the refractive index of a liquid 7-5 between them is set to 1.333. Here, since light is required to be incident on the surfaces of the first substrate and the second substrate almost vertical thereto and the reflected light is detected in this geometry, the incident angle of the incident light is set to 0°. In the figure, a solid line D shows a reflection spectrum in the case of absence of the target layer 7-4 on the both substrate; a dashed line D' shows a reflection spectrum in the case of presence of the target layer 7-4 on the both substrates. Since a difference in optical path length between reflected light beams generated on respective surfaces of the first substrate 7-1 and the second substrate 7-2 facing each other is approximately 600 nm, the minimum in the reflection spectrum appears in the vicinity of a wavelength of 600 nm. The figure shows that a wavelength position giving the minimum in the reflection spectrum shifted to a short wavelength side by the binding with the target. This is because reflection of light occurs on the surface of the respective layers of the biochemical substance added on the first substrate 7-1 and the second substrate 7-2, not on the surfaces of the first substrate 7-1 and the second substrate 7-2, and accordingly the difference in optical path length becomes shorter than that in the case of absence of the layers of the biochemical substance, which causes a change in the intensities of the reflected light at wavelengths. The magnitude of the wavelength shift at this time is 53.3 nm, being about 4 times the magnitude of the wavelength shift of the nonpatent document 2. Thus, the binding of the target with the probe can be detected with high sensitivity while the amount of specimen required to fill the cell, i.e., the amount of specimen consumed by the measurement is decreased by reducing the thickness of the cell.

Figure 9:
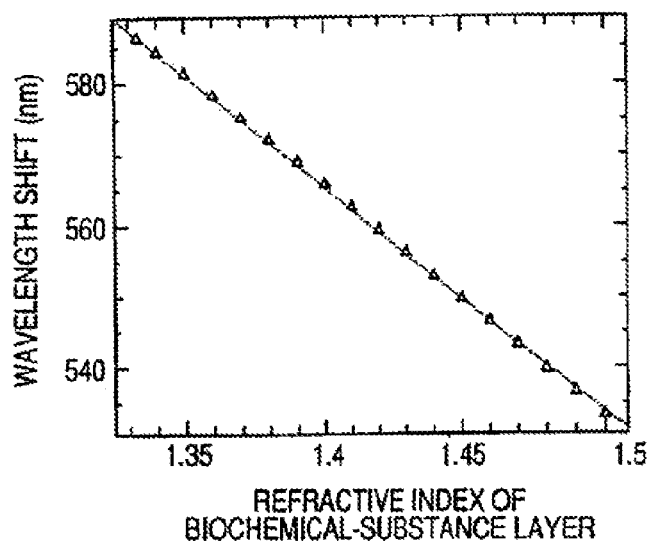
FIG. 9 is a diagram showing a relation between the refractive index of the layer of a biochemical substance and the wavelength shift.

Moreover, gradual variation of the refractive index as well as the determination as to whether there is the layer of a biochemical substance of a refractive index of 1.5 can be measured. FIG. 9 shows a variation of a wavelength giving the minimum in the reflection spectrum when the refractive index of the target layer is varied from 1.333 to 1.5. It can be seen from the figure that the wavelength position giving the minimum in the reflection spectrum varies almost linearly to variation of the refractive index. Here, this gradual change of the refractive index corresponds to a gradual change of the density of the binding of the target. This correspondence relation can be explained, for example, by an effective medium approximation of the Lorentz-Lorenz theory that is described in a paper by M. Harris, et al., Thin Solid Films, 1979, 57, 173-178, or the like. From the foregoing, the gradual change of the density of the binding of a biochemical substance can be measured as a change of the wavelength shift.

On the other hand, assumption of the thickness of the layer of a biochemical substance is done corresponding to the size of the biochemical substance that is considered. The thickness of the layer of the biochemical substance was assumed 10 nm in this embodiment. The magnitude of the wavelength shift is in proportion to the layer thickness of this biochemical substance. For example, if a smaller biochemical substance is considered and the thickness of the layer of a biochemical substance is assumed to be 1 nm, the magnitude of the wavelength shift will become 1/10 of a value when assuming the thickness to be 10 nm.

In the case where the separation between the substrates is specified to be 240 nm, the minimum in the reflection spectrum that appears in the vicinity of a wavelength of 600 nm is caused by first-order optical interference. Thus, for improvement in detection sensitivity, it is desirable to set the separation between the first and second substrates to a separation where the minimum in the reflection spectrum by low-order optical interference appears in a wavelength band of light used for the measurement. The reason will be explained below.

Figure 10:
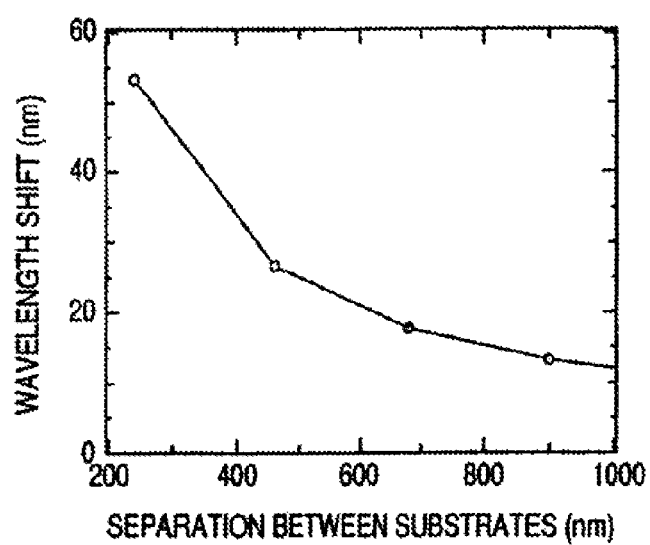
FIG. 10 is a diagram showing a relation between the separation between substrates and the wavelength shift of the reflection spectrum.

Since when the separation between the substrates is set to two times 240 nm, i.e., 480 nm, a difference in optical path length between the reflected light beams generated on respective surfaces of the first substrate 7-1 and the second substrate 7-2 facing each other is approximately 1200 nm, the minimum in the reflection spectrum appears in the vicinity of a wavelength of 600 nm by second-order optical interference. When the separation between the substrates is set to three times 240 nm, i.e., 720 nm, the minimum in the reflection spectrum appears in the vicinity of a wavelength of 600 nm by third-order optical interference. FIG. 10 show a plot of a relation of the magnitude of the wavelength shift of a minimum position in the reflection spectrum in the vicinity of a wavelength of approximately 600 nm obtained when the target forms bond with the probe versus the magnitude of the separation between the first and second substrates. Here, the layers of the biochemical substance that was targeted were assumed to have a refractive index of 1.5 and a thickness of 10 nm. As can be understood from FIG. 10, the magnitude of the wavelength shift of the minimum position in the reflection spectrum obtained when the target forms bond with the probe is in inverse proportion to the magnitude of the separation between the first and second substrates. For example, when this separation between the substrates is 240 nm, the magnitude of this wavelength shift was 53.3 nm, while when this separation between the substrates is increased to a double, i.e., 480 nm, the magnitude of this wavelength shift becomes a half, i.e., 26.7 nm. If the order n of optical interference further increases, the magnitude of the wavelength shift will become one n-th. From the above, using optical interface of a low order is advantageous for higher sensitivity.

Figure 1:
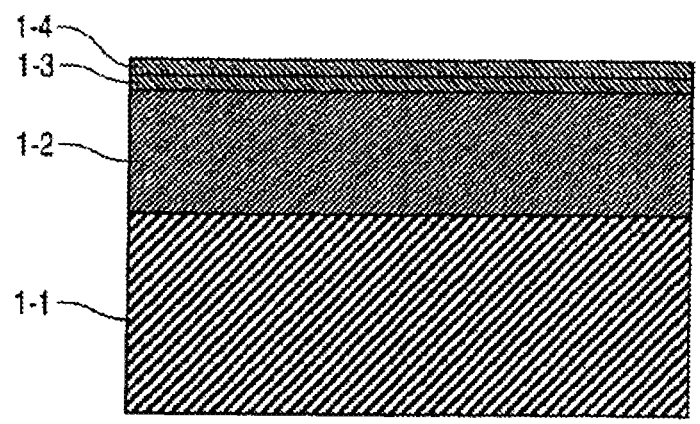
FIG. 1 is a diagram showing a structure of the conventional biochemical sensor.
Figure 2:
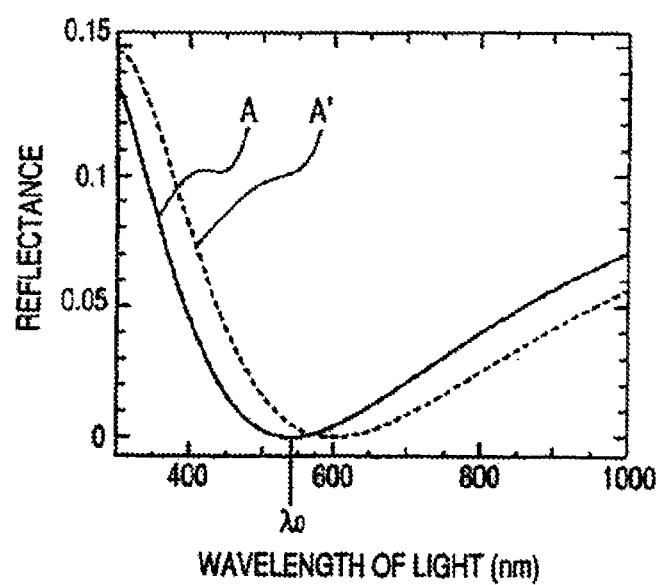
FIG. 2 is a diagram showing an interference color change of the conventional biochemical sensor.
Figure 3:
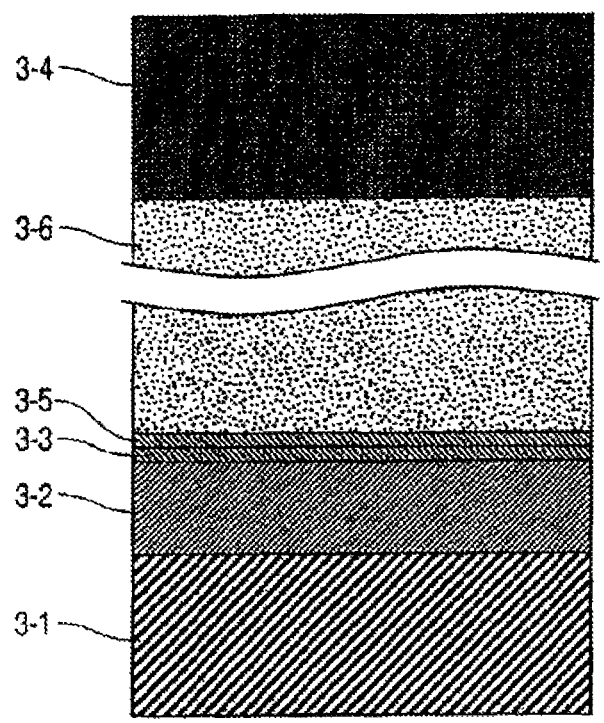
FIG. 3 is a diagram showing a structure of the conventional biochemical sensor.
Figure 4:
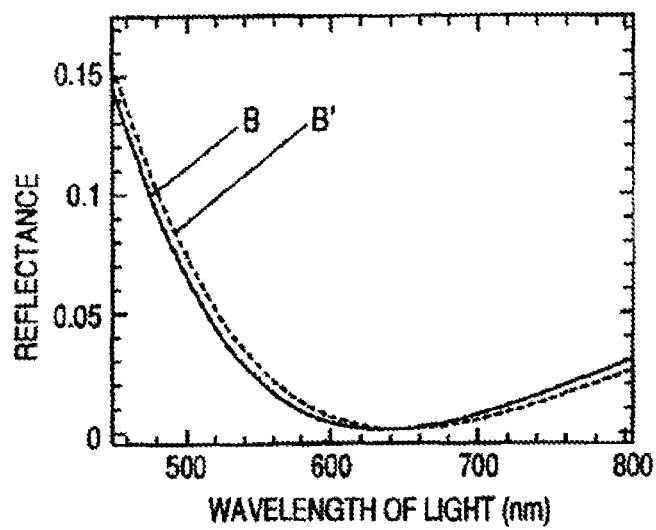
FIG. 4 is a diagram showing an interference color change of the conventional biochemical sensor.
Figure 5:
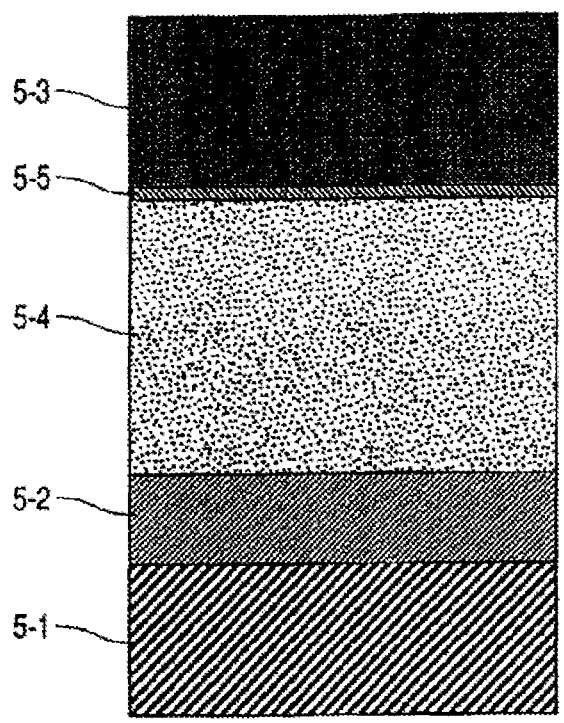
FIG. 5 is a schematic diagram of a sensor on whose optical window a biochemical substance adsorbs.
Figure 6:
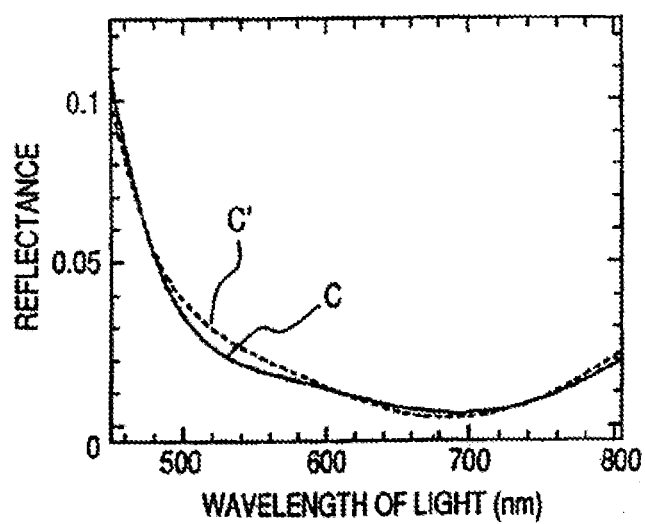
FIG. 6 is a diagram showing a change in a reflection spectrum caused by adsorption of the biochemical substance on the optical window.
Figure 11:
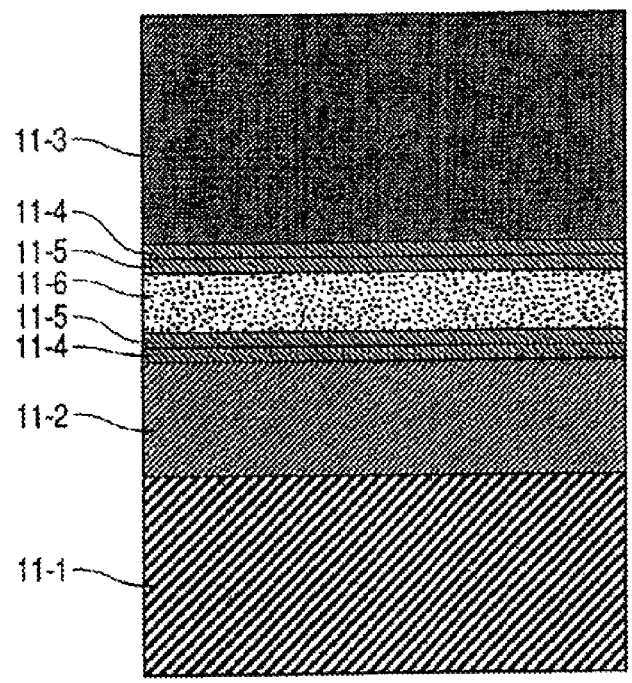
FIG. 11 is a schematic diagram showing other example of the biochemical sensor according to this invention.
Figure 12:
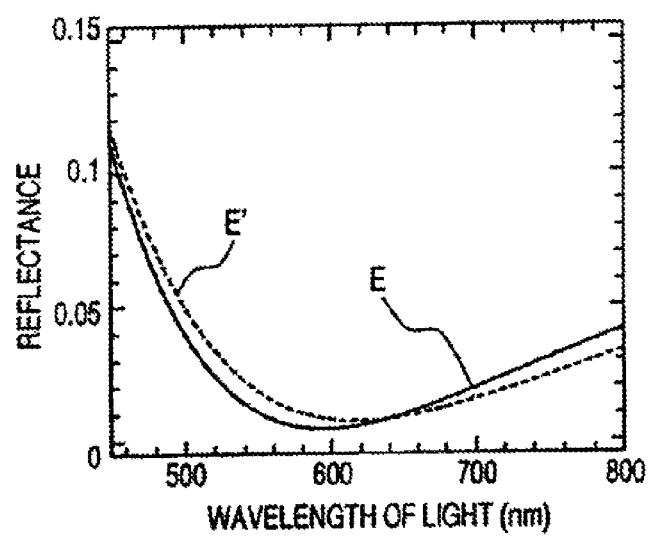
FIG. 12 is a diagram showing a calculation result of the reflection spectrum.

In addition, even when the optical thin film is formed on one of the substrates, as shown in FIG. 5, high-sensitivity measurement is realizable by immobilizing the probe not only on the surface of the optical thin film but also on the surface of the optical window and bringing the optical thin film closer to the optical window than the foregoing case. As shown in FIG. 11, an optical thin film 11-2 of a thickness of 70 nm and a refractive index of 2.2 is formed on a silicon substrate 11-1. By the presence of this optical thin film 11-2, the minimum in the reflection spectrum appears in the vicinity of a wavelength of 600 nm that corresponds to four times the optical thickness. An optical window 11-3 is formed above this optical thin film 11-2. The separation from the surface of this optical thin film 11-2 to the optical window 11-3 is set to 50 nm. Moreover, probes are provided on the surface of the optical thin film 11-2 and the surface of the optical window 11-3, respectively. FIG. 12 show a calculation result of the reflection spectrum in the case where layers 11-4 of the probe and layers 11-5 of the target are specified to have each a refractive index of 1.5 and a thickness of 10 nm and a liquid 11-6 therebetween is specified to have a refractive index of 1.333. A solid line E of FIG. 12 represents a reflection spectrum in the case of absence of the layer 11-5 of the target; a dashed line E' of FIG. 11 represents a reflection spectrum in the case of presence of the layer 11-5 of the target. The graphs show that the biding of the biochemical substance shifts a wavelength position giving the minimum in the reflection spectrum to a long wavelength side. The magnitude of this wavelength shift is 23.1 nm, which is 1.7 times the magnitude of a shift of the nonpatent document 2. This increase of the signal is attributed to a fact that addition of the layer 11-5 of the target on the optical window 11-3 contributes to the wavelength shift because of setting the separation between the surface of the optical thin film 11-2 and the optical window 11-3 to 50 nm. Thus, the binding of the target with the probe can be detected with high sensitivity. Note that it is preferable that the separation between the substrate of the optical thin film and the substrate of the optical window is 10 nm or more considering the size of a protein that is the probe or a protein that is targeted.

As described above, the binding of the target with the probe can be detected with high sensitivity without using a label in a state where the probe is immobilized on the surfaces of the both substrates, thereby decreasing the separation between the substrates, i.e., in a state where the volume of the cell is made smaller.

DESCRIPTION OF PREFERRED EMBODIMENTS OF THE INVENTION

First Embodiment

Hereafter, an embodiment of a simple cell for biochemical analysis and a simple biochemical analyzer of this invention that uses optical interference will be described.

Figure 13A:
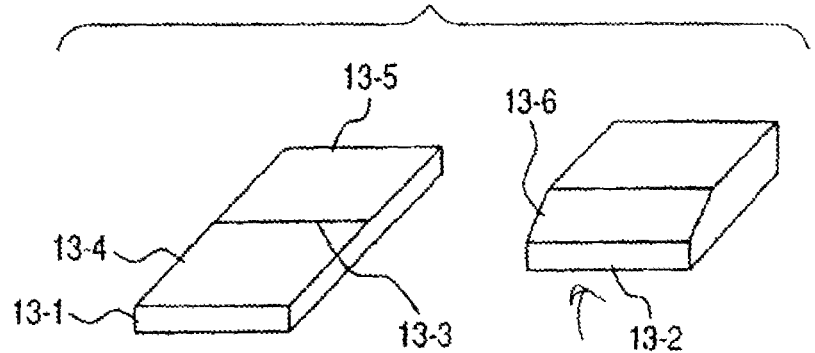

First, a production method of a kit for biochemical analysis will be explained. FIG. 13 shows a production method of the kit for biochemical analysis. As shown in FIG. 13A, a first substrate 13-1 and a second substrate 13-2 having a flat plane are prepared. The first substrate 13-1 and the second substrate 13-2 can be made of a transparent glass. A vertical elevation 13-3 of approximately 240-nm height is formed in the first substrate 13-1, and a flat plane 13-5 is made higher by 240 nm than a flat plane 13-4 beforehand. The second substrate 13-2 is provided with a plane 13-6 nonparallel to the flat plane on the opposite side thereof beforehand. The flat plane 13-4 of the first substrate 13-1 and the flat surface of the second substrate are silane-coated using 3-aminopropyltrimethoxysilane. Since the surface subjected to this processing is hydrophilic, an aqueous solution can be introduced into a cell formed between the first substrate and the second substrate by capillarity. Moreover, a biochemical substance can be immobilized using an amino group introduced by this processing. For example, in order to immobilize a protein as the probe, a protein carboxyl group and an amino group introduced on the surface can be brought into amide binding using an aqueous solution of N-hydroxysucciimide and water soluble carbodiimide. Alternatively, performing silane coating on the flat plane 13-4 of the first substrate 13-1 and the flat surface of the second substrate 13-2 using 3-glycidoxypropyltrimethoxysilane also makes it possible to obtain hydrophilic surfaces similarly. Moreover, using an epoxy group introduced by this processing, a biochemical substance can be immobilized by dehydrating condensation with the amino group or a hydroxyl group.

Note that a pair of the first substrate 13-1 and the second substrate 13-2 with probes immobilized thereon may be offered as a kit for biochemical analysis, or such a pair with probes not immobilized thereon may be offered as a kit for biochemical analysis, leaving immobilization of the probes to the user.

Figure 13B:
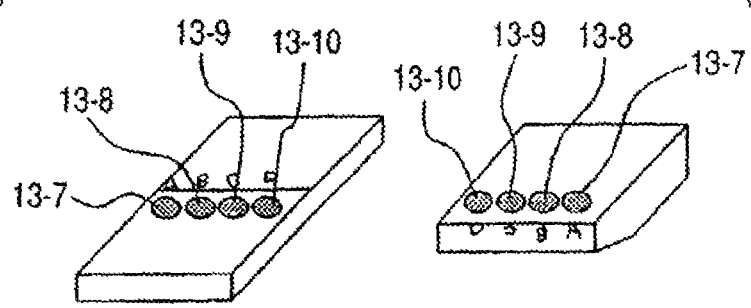
Figure 13C:
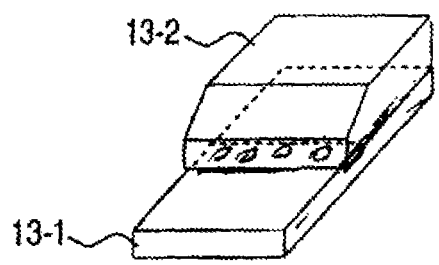

Next, as shown in FIG. 13B, probes 13-7, 13-8, 13-9, and 13-10 are immobilized on the flat plane 13-4 of the first substrate 13-1 and the flat surface of the second substrate 13-2. At this time, positions at which the probes are immobilized are so determined that, when the substrates are faced each other, the sites on which the same kind of probe is immobilized face each other. Moreover, at this time, the probe is intended to be immobilized on the opposite side of the nonparallel plane 13-6 in the substrate 13-2. After the probe is immobilized, as shown in FIG. 13C, the planes on which the probes are immobilized are faced each other, and the substrates are fixed to each other with a cramp etc. in a state where the flat plane 13-5 of the first substrate 13-1 and the flat plane of the second substrate 13-2 contact with each other. By this process, a gap with a vertical elevation 13-3 in a height direction is formed between the planes on which the probe is immobilized, respectively, and thus the cell can be formed.

Figure 14:
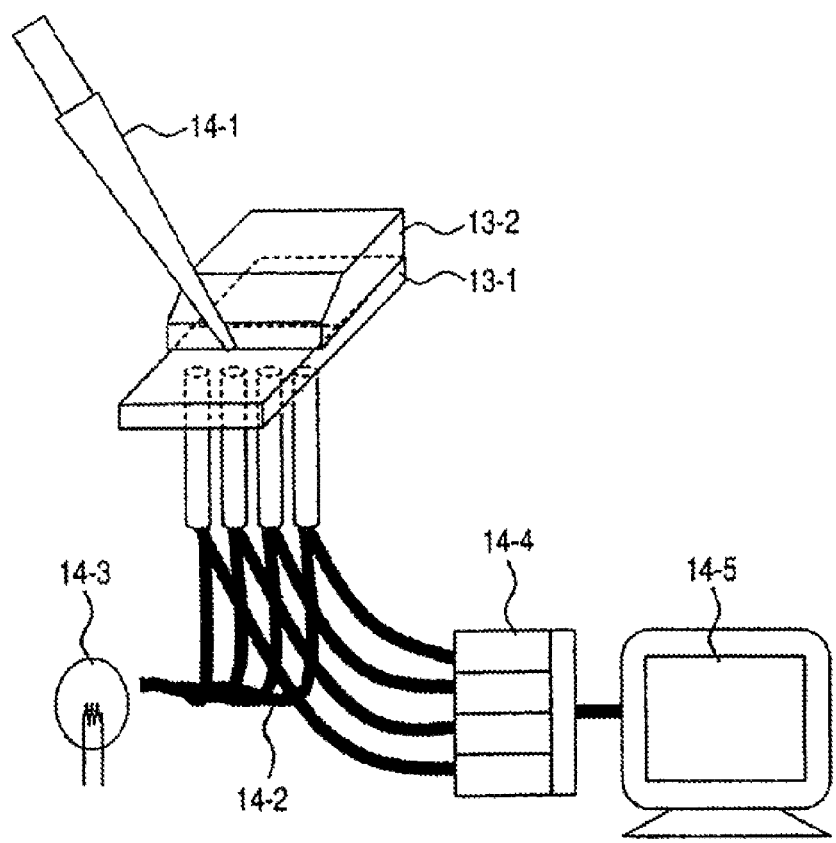
FIG. 14 a schematic diagram showing one example of a detection unit of the biochemical analyzer according to this invention.

One example of a procedure of detecting the binding of the target with the probe of this kit for biochemical analysis will be shown below. FIG. 14 is a schematic diagram showing one example of a detection unit of a biochemical analyzer according to this invention. In order to introduce a specimen solution into the cell formed between the first substrate 13-1 and the second substrate 13-2 that are fixed with a clamp etc., a mechanical pipet 14-1 is used to drop the specimen solution near the cell. The specimen solution dropped near the cell is introduced into the cell by capillarity. The binding of the target introduced into the cell and the probe immobilized on the surfaces of the first substrate 13-1 and the second substrate 13-2 is measured by an optical detection system below. Using a light guide 14-2 made up of an optical fiber bundle, light from a white light source 14-3 is irradiated from the first substrate 13-1 side, and the reflected light from the surfaces of the first substrate 13-1 and the second substrate 13-2 on each of which the probe is immobilized is guided to respective spectrometers 14-4. A computer 14-5 captures each reflection spectrum in real time, calculates a wavelength giving a minimum in each reflection spectrum, and performs display and recording of its temporal change in real time.

Figure 15:
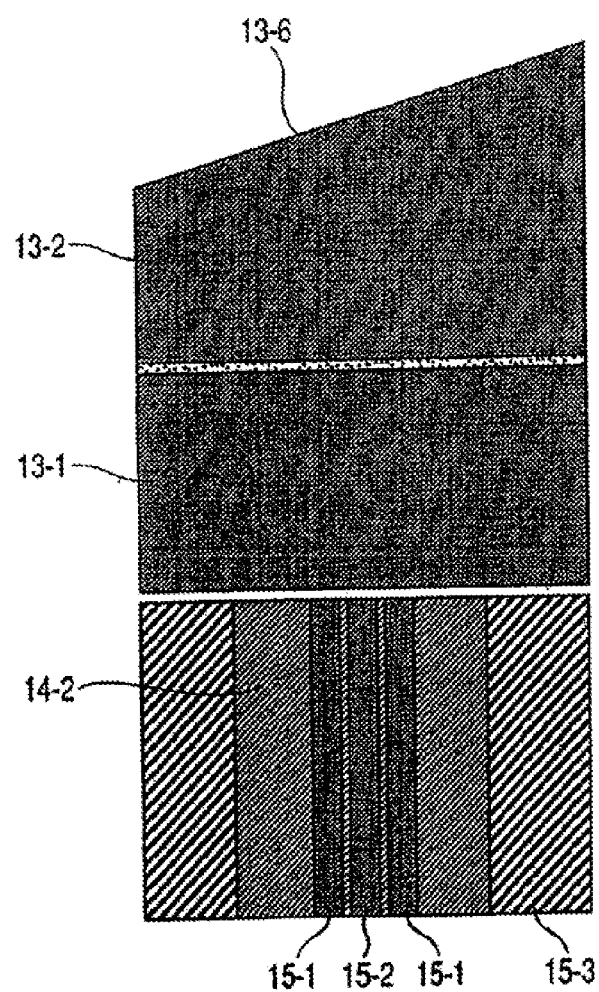
FIG. 15 is a partial enlarged view of a cell for biochemical analysis being set in the biochemical analyzer.

FIG. 15 is a partial enlarged view of the biochemical sensor installed in the biochemical analyzer, showing a sectional view of the light guide 14-2, a stage 15-3 on which the light guide 14-2 is fixed, the first substrate 13-1, and the second substrate 13-2. The light guide 14-2 consists of an optical fiber bundle in which strands of optical fiber 15-1 to guide the light from the light source are tied to surround optical fiber 15-2 to guide the light to the spectrometer. As shown in FIG. 15, the point of the light guide 14-2 and the first substrate 13-1 are arranged to almost touch each other. This disposition can prevent the reflected light from the back of the first substrate from directly entering the optical fiber 15-2 for guiding the reflected light to the spectrometer. Moreover, since the nonparallel plane 13-6 that is an upper plane of the second substrate 13-2 is inclined, the reflected light from the nonparallel plane 13-6 can be prevented from directly returning to the optical fiber 15-1. Alternatively, the same effect can be obtained by placing an antireflective coating on the plane 13-6 to prevent the reflection itself of the light on the plane 13-6. Further alternatively, by specifying the substrate 13-2 to be made of an optical absorbing glass, such as a black glass, the transmitted light in the substrate 13-2 that is a part of the light irradiated from the optical fiber 15-2 is made to be absorbed in the substrate 13-2. Therefore, the effect on the measurement caused by the transmitted light entering the optical fiber 15-2 for guiding the reflected light to the spectrometer after being reflected on the interface can be avoided. Moreover, by specifying the substrate 13-2 to be made of a black glass, the effect on the measurement caused by the indoor light entering the optical fiber 15-2 for guiding the reflected light to the spectrometer can be avoided.

Figure 16:
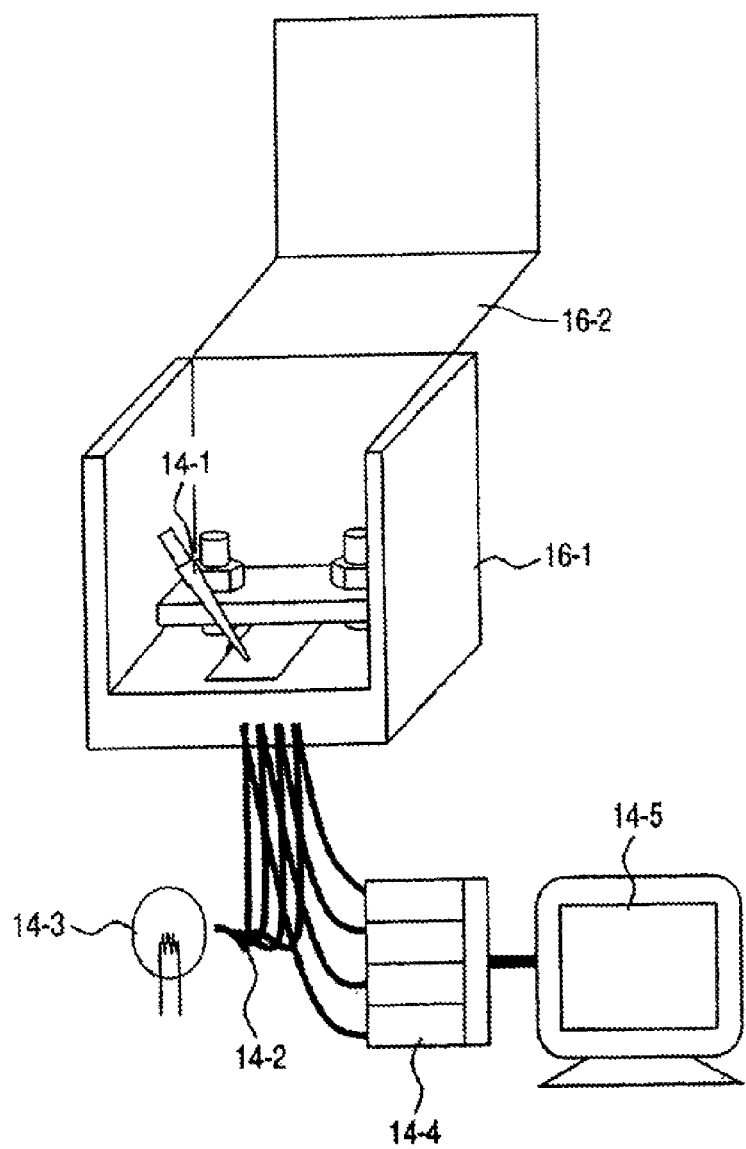
FIG. 16 is a partial enlarged view of the biochemical analyzer.

FIG. 16 shows one example of the biochemical analyzer for performing the above measurement. The biochemical analyzer is provided with a black box 16-1 for housing the first substrate 13-1, the second substrate 13-2, the mechanical pipet 14-1, a point of the light guide 14-2, and the stage 15-3 in it. By using this black box 16-1, the effect on the measurement caused by the indoor light entering the optical fiber 15-2 for guiding the reflected light to the spectrometer can be avoided. The black box 16-1 is provided with a lid 16-2. Setup is done with the lid 16-2 opened and the measurement is performed with the lid 16-2 closed. The black box is further provided with a clamp for fixing the first substrate 13-1 and the second substrate 13-2 in it.

Figure 17:
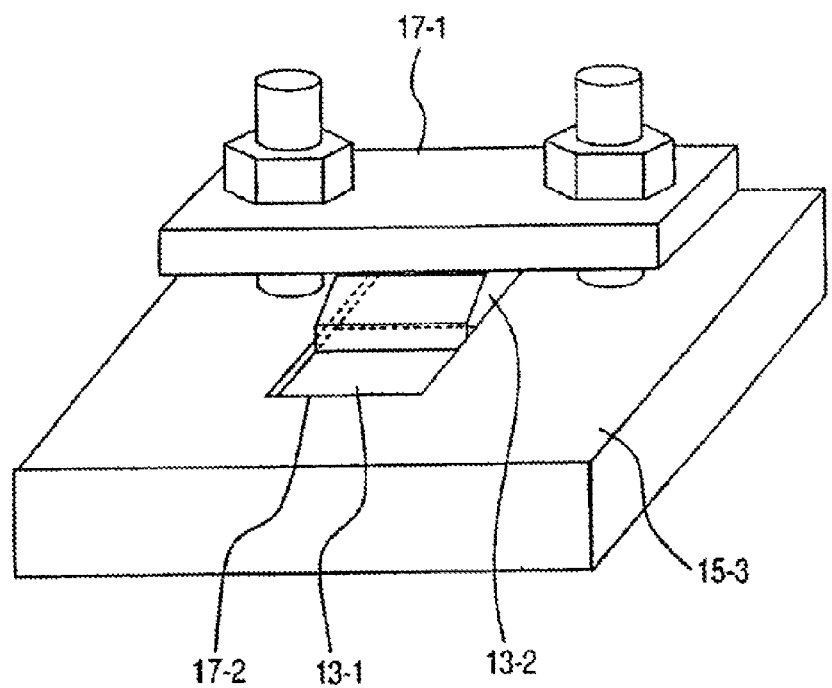
FIG. 17 is a schematic diagram of one example of a cramp and its surroundings.

FIG. 17 is a schematic diagram of one example of the clamp and its surroundings. The illustrated clamp fixes the first substrate 13-1 and the second substrate 13-2 by sandwiching them with the stage 15-3 and a board 17-1, and pressing down the board 17-1 with screws. A groove 17-2 into which the first substrate 13-1 and the second substrate 13-2 is settable is formed in the stage 15-3. The form of the groove 17-2 shall be such that its width just accommodates the first substrate 13-1 and its depth houses the whole of the first substrate 13-1 and a part of the second substrate 13-2, the first substrate 13-1 and the second substrate 13-2 being combined with each other. Moreover, the position of this groove 17-2 is so adjusted that the points of the light guide 14-2 come exactly under the positions at which the probes 13-7, 13-8, 13-9, and 13-10 are fixed. The light source 14-3, points of the light guide 14-2 on the light source side and on the spectrometer side, the spectrometers 14-4, and the computer 14-5 are placed and used outside the black box.

Second Embodiment

Figure 18A:
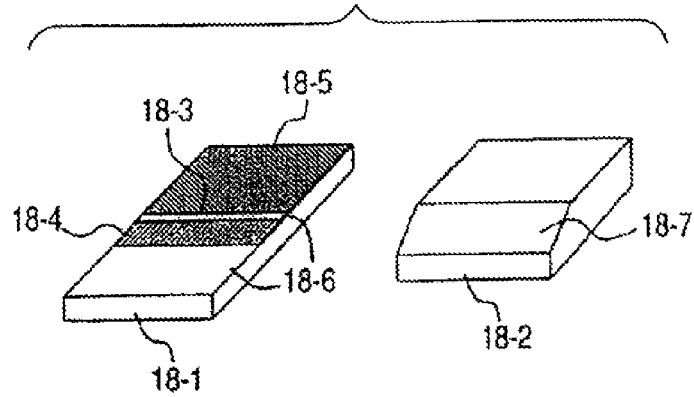

Although the substrate is specified to be made of a glass in the first embodiment, the kit for biochemical analysis can be produced with resins, such as polystyrene and PDMS. FIG. 18 shows a production method of a kit for biochemical analysis in the case where a resin is used for a substrate. As shown in FIG. 18A, a first substrate 18-1 and a second substrate 18-2 having a flat plane are prepared. In this embodiment, the substrate 18-1 and the substrate 18-2 are specified to be made of transparent polystyrene. As shown in FIG. 18A, the first substrate 18-1 is provided with a vertical elevation 18-3 of 240-nm height and a member 18-4 for keeping the separation between the first substrate 18-1 in which a wall of approximately 240-nm height and 80-nm width are arranged in a period of 400 nm and the other substrate. Note that, with the help of the vertical elevation 18-3, a flat plane 18-5 of the substrate 18-1 is made higher than the other flat plane 18-6 by 240 nm. Like the first embodiment, a plane 18-7 nonparallel to the flat plane and opposite to it is provided on the second substrate 18-2.

The vertical elevation of the first substrate 18-1 and the member 18-4 for keeping the separation can be manufactured by a method that will be described below. FIG. 19 is a production process diagram of a kit for biochemical analysis using a nanoimprint method in this embodiment. As shown in FIG. 19A, a raw material 19-1 made from polystyrene (26 mm×40 mm, and 1 mm in thickness) and a metal mold 19-2 made from nickel are prepared. As shown in FIG. 19B, this raw material 19-1 and the nickel-made metal mold 19-2 heated to 150° C. are pressed for 10 seconds with a press pressure of 25 MPa. Then, by separating the metal mold 19-2 from the substrate 19-1 perpendicularly, the substrate 18-1 that has the vertical elevation 18-3 of 240-nm height and the member 18-4 for keeping the separation between the substrates can be obtained, as shown in FIG. 19C. FIG. 19D shows an enlarged view of the member 18-4 for keeping the separation between the substrates. The height F of a wall is approximately 240 nm, the width G of the wall is 80 nm, and the period H of its array is 400 nm. Here, an arrow 19-3 of FIG. 19C and an arrow 19-4 of FIG. 19D show the same direction.

FIG. 20 shows a method for manufacturing the metal mold 19-2. A master material 20-1 shown in FIG. 20A is a silicon wafer of a crystal orientation (100) and dimensions of 26 mm×40 mm. As shown in FIG. 20B, a photoresist 20-2 is applied on the master material 20-1 and the photoresist (resist) located at the vertical elevation and the wall is subjected to exposure by an electron beam writing system. Subsequently, as shown in FIG. 20C, the resist of an exposed portion is removed by a development process. In a photoresist remaining portion 20-3 shown by the hatched area of FIG. 20C, the resist in the whole hatched area is remained, while in a resist remaining portion 20-4 shown by another hatched area, the resist is remained partly as in the form of a grid. FIG. 20D is an enlarged view of a grid-like pattern in the portion 20-4 where the resist remains. The width and the period of a grid 20-6 of this resist are the same as the values of G and H shown in FIG. 19D. An arrow 20-7 shows the same direction as an arrow 20-5 of FIG. 20C. Next, as shown in FIG. 20E, dry etching is used to form a metal mold master 20-8 in which a shape corresponding to the vertical elevation and the wall is formed. FIG. 20F is an enlarged view of an area 20-9 in which the array of walls formed by dry etching. The width and the period of a wall 20-11 of FIG. 20F are the same as G and H shown in FIG. 20D. An arrow 20-12 shows the same direction as an arrow 20-10 of FIG. 20E. Subsequently, as shown in FIG. 20G, a nickel thin film is formed on the metal mold master 20-8 by an electroless plating method, and then the nickel thickness is increased to 1 mm by an electrolytic plating method to form a metal mold 20-13. Subsequently, by performing separation processing with a predetermined fluorinated agent on the surface of the metal mold 20-13, a metal mold 20-16 that has a mold 20-14 of the vertical elevation of 240-nm height shown in FIG. 20H and a mold 20-15 of the member for keeping the separation between the substrates can be obtained.

Figure 21:
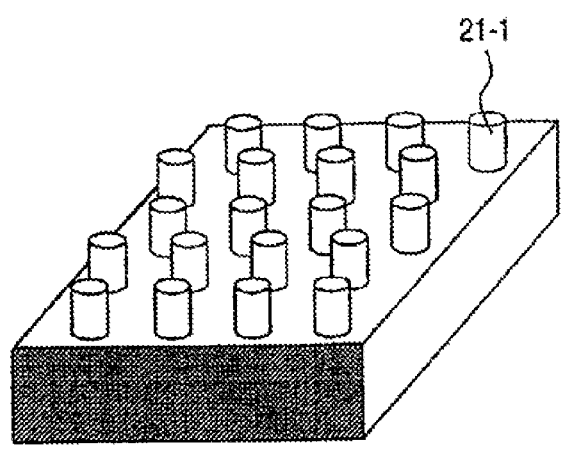
FIG. 21 is a diagram showing an example of a member for keeping a separation between substrates.

Although in this embodiment, the vertical elevation and the array of walls were formed using polystyrene as a raw material by a nanoimprint method, other molding methods, including the cast method of pouring a liquid material onto a metal mold, can also be used. Especially when PDMS that is transparent and adheres to the substrate is used, it is preferable to use the cast method. Moreover, although in this embodiment, the member 18-4 for keeping the separation between the substrates was specified to be the array of walls, members of other shapes, such as of an array of cylinders 21-1 as shown in FIG. 21, may be used.

Figure 18B:
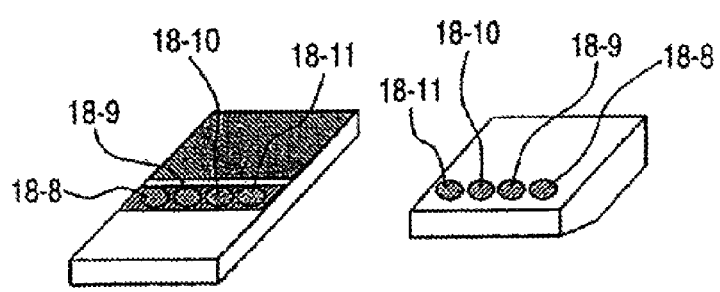
Figure 18C:
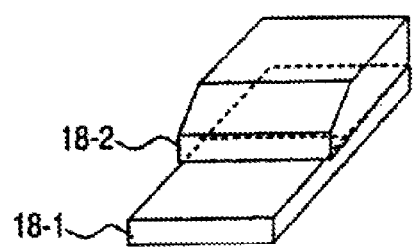
Figure 20A:
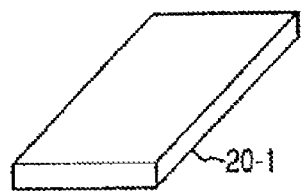
Figure 20E:
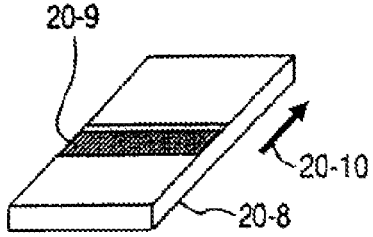
Figure 20B:
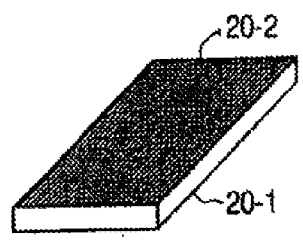
Figure 20F:
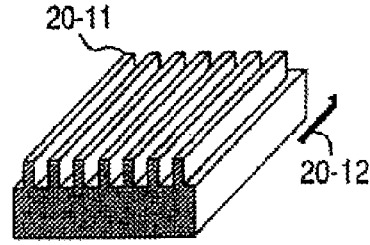
Figure 20C:
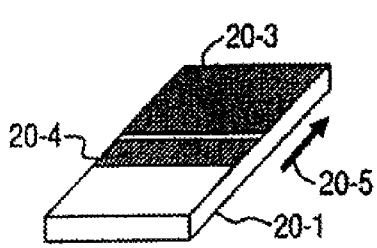
Figure 20G:
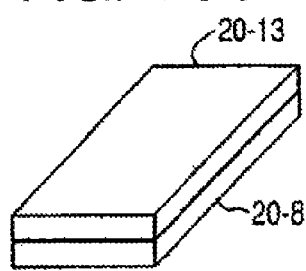
Figure 20D:
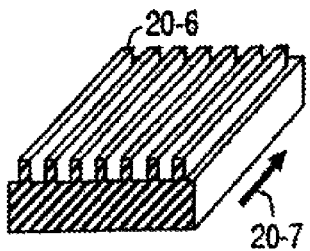
Figure 20H:
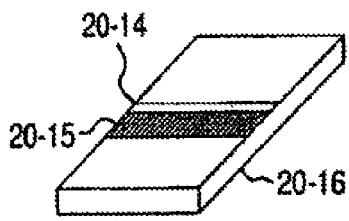

Returning to FIG. 18, after preparing the first substrate 18-1 and the second substrate 18-2, the area 18-4 of the first substrate 18-1 and the flat plane of the second substrate 18-2 are silane-coated using 3-aminopropyltrimethoxysilane. Since the surface subjected to this processing is hydrophilic, an aqueous solution can be introduced into a cell formed in a gap between the first substrate and the second substrate by capillarity. Moreover, a biochemical substance (probe) can be immobilized using an amino group introduced by this processing. Alternatively, like the first embodiment, a hydrophilic surface is obtained by silane-coating the surface of the substrate using 3-glycidoxypropyltrimethoxysilane, whereby, as well as by the use of an epoxy group introduced by this process, a biochemical substance can be immobilized. Then, as shown in FIG. 18B, probes 18-8, 18-9, 18-10, and 18-11 are immobilized on the area 18-4 of the first substrate 18-1 and the surface of the second substrate 18-2. At this time, positions at which the probes are immobilized are so determined that the sites on which the same kind of probe is immobilized face each other when the substrates are faced each other. After the probe is immobilized, the planes on which the probe is immobilized are faced each other, as shown in FIG. 18C, and the substrates are fixed with a cramp like the first embodiment. By this fixing, a cell whose height is kept by the member for keeping the separation between the substrates can be formed between the planes on which the probe is immobilized, respectively. Incidentally, in the case where a material having a self-adhesion property is used for either the first substrate 18-1 or the second substrate 18-2, or used for the both the first substrate 18-1 and the second substrate 18-2, a state where the first substrate 18-1 keeps adhering to the second substrate 18-2 can be maintained without using the cramp.

Note that a pair of the first substrate 18-1 and the second substrate 18-2 with probes immobilized thereon may be offered as a kit for biochemical analysis, or such a pair with probes not immobilized thereon may be offered as a kit for biochemical analysis, leaving immobilization of the probes to the user.

Detection of the binding of the target with the probe of this cell for biochemical analysis is possible by using the same biochemical analyzer and the same measurement procedure as those of the first embodiment. Moreover, like the first embodiment, by specifying the second substrate 18-2 to be black-colored, the light transmitted in the second substrate 18-2 that is a part of the light irradiated from the optical fiber 15-1 is absorbed in the second substrate 18-2, which can avoid the effect on the measurement caused by the transmitted light entering the optical fiber 15-2 for guiding the reflected light to the spectrometer after being reflected on the interface. Furthermore, by specifying the second substrate 18-2 to be light absorbing, such as of black color, the effect on the measurement caused by the indoor light entering the optical fiber 15-2 for guiding the reflected light to spectrometer can be avoided without using the black box.

Third Embodiment

In the first embodiment and the second embodiment, the specimen solution is introduced into the cell using capillarity. The binding of the target with the probe can also be measured as follows: A space formed between the substrates is used as a flow cell and a state where the specimen solution flows in the cell regularly is made, for example, by applying a pressure to it. This embodiment explains an example of the case where a space formed between the substrates is used as the flow cell.

Figure 22A:
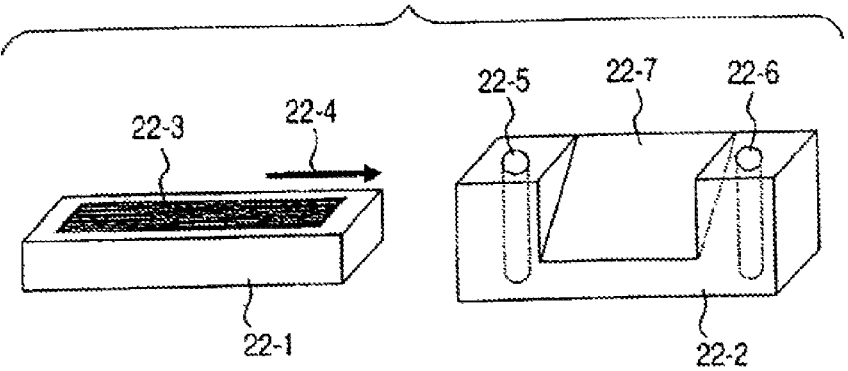

FIG. 22 is an explanatory diagram about a production method of a kit for biochemical analysis in the case where a gap for holding a specimen solution is specified to be the flow cell. As shown in FIG. 22A, a first substrate 22-1 and a second substrate 22-2 having a flat plane are prepared. The first substrate 22-1 and the second substrate 22-2 are specified to be made of PDMS. As shown in FIG. 22A, the first substrate 22-1 is provided beforehand with an area 22-3 having an array of slots that is intended to form a gap between the substrates and is obtained by arranging slots each having a depth of 240 nm and a width of 320 nm in a period of 400 nm. FIG. 23 is an enlarged view the array of slots for keeping this separation between the substrates. The depth J of the groove is approximately 240 nm, the width K of the groove is 320 nm, and the period L of its array is 400 nm. Here, an arrow 22-4 of FIG. 22 and an arrow 23-1 of FIG. 23 show the same direction. On the other hand, holes 22-5, 22-6 each for allowing a tube for applying a pulling pressure to the array of slots to be connected are formed beforehand in the second substrate 22-2. Moreover, like the first embodiment and the second embodiment, on the opposite side of the flat plane of the second substrate 22-2, a plane 22-7 nonparallel to the flat plane to avoid the effect of the reflected light is provided beforehand.

Incidentally, it is not necessarily required to form the array of slots in the area 22-3 of the first substrate. In the case where the array of slots is not formed in the area 22-3, the area 22-3 becomes a flat plane depressed from a surrounding plane by approximately 240 nm.

Figure 22B:
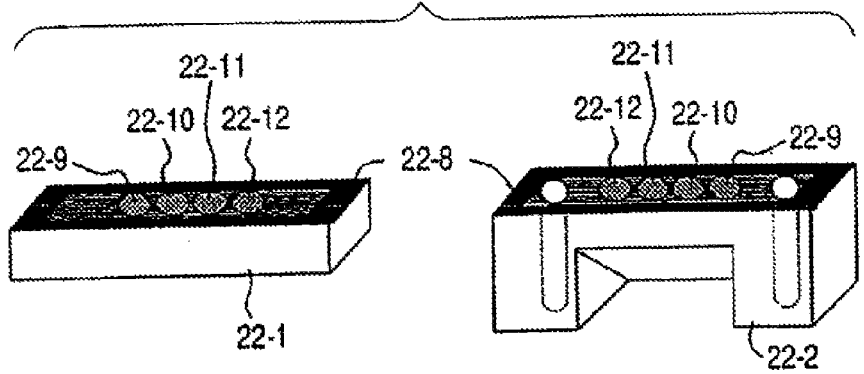
Figure 22C:
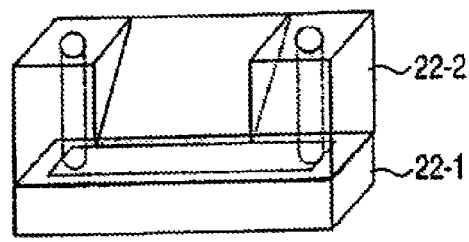
Figure 23:
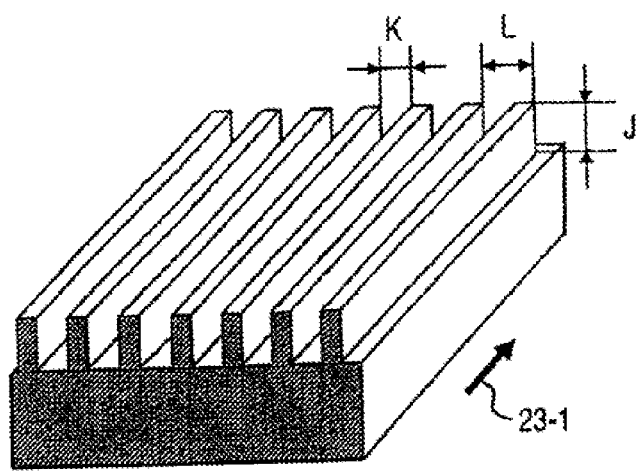
FIG. 23 is an enlarged view of an array of slots for keeping the separation between the substrates.

A mask 22-8 is given by sticking a film of a resin that has a property of self-adhesion to PDMS, as shown in FIG. 22B, after preparing the first substrate 22-1 and the second substrate 22-2. The area 22-3 of the first substrate 22-1 in which the slots are formed and a part of the flat plane of the second substrate that is not masked are subjected to silane-coating using 3-aminopropyltrimethoxysilane. Since the surface subjected to this processing is hydrophilic, an aqueous solution can be introduced into a cell formed between the first substrate and the second substrate by capillarity. Moreover, a biochemical substance (probe) can be immobilized using an amino group introduced by this processing. Alternatively, like the first embodiment, a hydrophilic surface is obtained by silane-coating the surface of the substrate using 3-glycidoxypropyltrimethoxysilane, whereby, as well as by the use of an epoxy group introduced by this process, a biochemical substance can be immobilized. Then, as shown in FIG. 22B, probes 22-9, 22-10, 22-11, and 22-12 are immobilized on the area 22-3 of the first substrate 22-1 in which the array of slots is formed and on the surface of the flat plane of the second substrate 22-2. At this time, positions at which the probes are immobilized are so determined that the sites on which the same kind of probe is immobilized face each other when the substrates are faced each other. Then, the mask 22-8 is removed from the first substrate 22-1 and the second substrate 22-2, and the first substrate 22-1 and the second substrate 22-2 are adhered using their property of self-adhesion, as shown by FIG. 22C.

Note that a pair of the first substrate 22-1 and the second substrate 22-2 with probes immobilized thereon may be offered as a kit for biochemical analysis, or such a pair with probes not immobilized thereon may be offered as a kit for biochemical analysis, leaving immobilization of the probes to the user.

Figure 24:
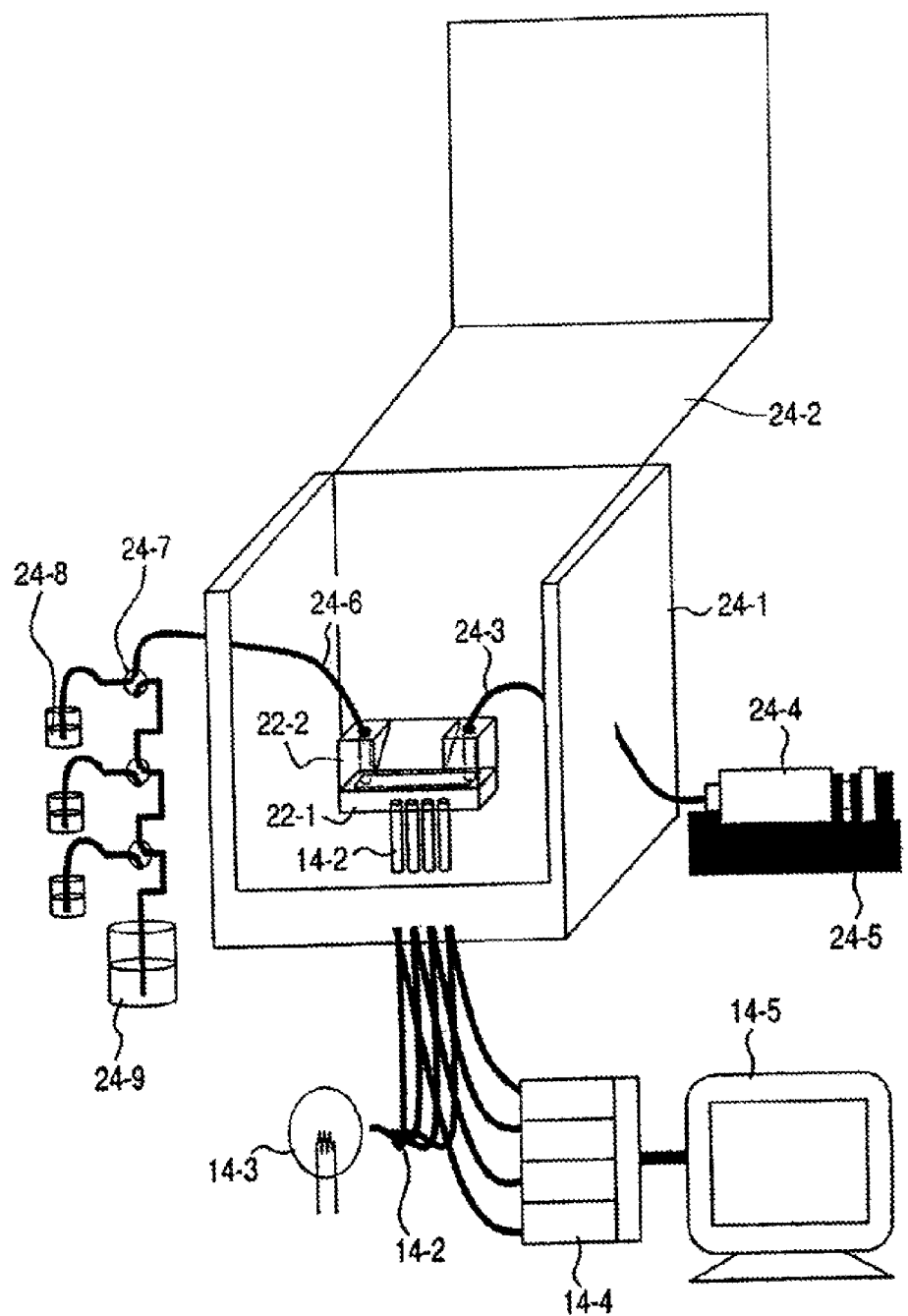
FIG. 24 is a schematic diagram of a biochemical analyzer using the flow cell.

FIG. 24 schematically shows an analyzer and a method for detecting the binding of a target with a probe using this kit of biochemical analysis. A tube 24-3 is connected to the hole 22-6 of the second substrate 22-2 for allowing a tube to be connected. A syringe 24-4 is connected to the opposite side of this tube 24-3. Using a syringe pump 24-5, the syringe is evacuated to apply a pulling pressure to the flow cell. A tube 24-6 is connected to the hole 22-5 of the second substrate for allowing another tube to be connected. A valve 24-7 is connected to the opposite side of this tube 24-6. By switching this valve 24-7, a state of sending a buffer solution 24-9 can be changed to a state of sending a specimen solution 24-8.

Moreover, plural valves are attached to the analyzer, as shown in FIG. 24. Furthermore, a dilute hydrochloric acid is put in one of the containers connected to the valve, and is injected into the flow cell for three minutes, whereby a biochemical substance (target) formed bond with the probe when each specimen solution is flown in the flow cell can be dissociated from the biochemical substance immobilized on the substrate as a probe. By this configuration, different specimen solutions can be injected into the flow cell continuously to be measured, as follows. First, a state of sending the buffer solution is switched to a state of sending the specimen solution. The buffer solution is sent again, and a shift of the minimum position in the reflection spectrum with respect to that of the initial state of sending the buffer solution is checked. Then, after dissociating the biochemical substance by sending the dilute hydrochloric acid for three minutes, the buffer solution is sent to return the system to its initial state. The above is defined as one cycle. Similarly next injection of a specimen solution can be performed.

The binding of the target in the specimen solution sent into the cell with the probes immobilized on the surfaces of the first substrate 22-1 and the second substrate 22-2 can be measured by the same optical detection system as that of the first embodiment. Using the light guide 14-2, the light from the white light source 14-3 is irradiated from the first substrate 22-1 side, and the reflected light from the surfaces of the first substrate 22-1 and the second substrate 22-2 on which the probes are immobilized is guided to the respective spectrometers 14-4. The computer 14-5 captures the reflection spectrum obtained from the each spectrometer 14-4 in real time, and reads changes of wavelengths giving minimums of the respective reflection spectra.

Like the first embodiment, a point of the light guide 14-2 is disposed to almost touch the first substrate 22-1. By this arrangement, the reflected light from the back of the first substrate is prevented from directly entering the optical fiber 15-2 for guiding the reflected light to the spectrometer. Moreover, since the nonparallel plane 22-7 of the second substrate 22-2 is inclined, the reflected light from the nonparallel plane 22-7 can be prevented from directly returning to the optical fiber 15-2. In the above measurement, the use of a black box 24-1 can avoid the effect on the measurement caused by the indoor light entering the optical fiber 15-2. The black box 24-1 is provided with a lid 24-2 and houses the light guide 14-2, the first substrate 22-1, the second substrate 22-2, the tube 24-3, and the tube 24-6. Setup is done with the lid 24-2 opened, and the measurement is performed with the lid 24-2 closed.

Note that if the second substrate is specified to be made of black PDMS, light that is transmitted in the second substrate 22-2 in the portion of the light irradiated from the optical fiber 15-1 is allowed to be absorbed in the substrate 22-2. By this scheme, an effect on the measurement caused by the transmitted light entering the optical fiber 15-2 for guiding the reflected light to the spectrometer after being reflected on an interface can be avoided. Moreover, by specifying the second substrate 22-2 to be made of the black PDMS, the effect on the measurement caused by indoor light entering the optical fiber 15-2 for guiding the reflected light to the spectrometer can be avoided without using the black box. Although the array of the slots shown in FIG. 23 was formed to form the cell in this embodiment, the following is also possible: Slits are formed in the area 22-3 of the first substrate 22-1, leaving an array of cylinders as shown in FIG. 21, and the first substrate thus formed is stuck to the second substrate 22-2 to shape a cell whose thickness is defined by the height of the cylinders. Moreover, although the probe and the light guide were arranged in a line in a solution sending direction in this embodiment, this may be changed to two or more lines to form a two-dimensional array.

Forth Embodiment

As described above, by forming an optical thin film whose optical thickness is ¼ of a wavelength of a visible light or its odd multiple on a single side of the substrate, it is possible to further reduce the dimension of the gap between the substrates than those of the first, second, and third embodiments, and decrease the capacity of the cell. An embodiment in the case where the thickness of the cell is further reduced by using an optical thin film will be explained below.

Figure 25A:
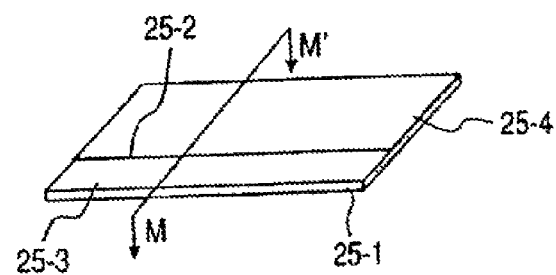
Figure 25B:
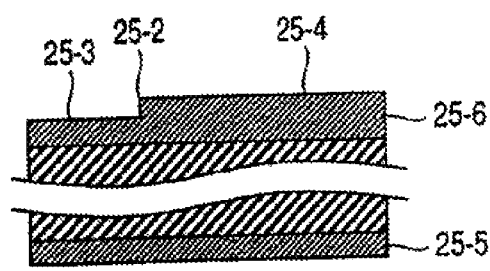

FIG. 25 is a diagram showing a manufacture procedure of the second substrate in the case of forming an optical thin film on the second substrate. As shown in FIG. 25A, a second substrate 25-1 on which a silicon-nitride thin film whose refractive index is adjusted to 2.2 is formed on a flat surface of a silicon substrate of 26 mm×10 mm is prepared. A silicon-nitride thin film is also formed on its back. With this film, chemical resistance of this substrate against alkaline solutions is improved. The vertical elevation 25-2 of 50-nm height is formed in this second substrate 25-1, and a flat plane 25-4 is made higher than a flat plane 25-3 by 50 nm beforehand. FIG. 25B shows a sectional view taken along the line M-M' of FIG. 25A. A silicon nitride film 25-5 is formed on the back of the silicon substrate. On the surface of the silicon substrate, a silicon nitride film 25-6 is formed. There is a vertical elevation 25-2 of 50-nm height in the silicon nitride film 25-6. A low plane defined by the vertical elevation 25-2 as a boundary is the flat plane 25-3, and a high plane defined similarly is a flat plane 25-4.

FIG. 26 shows a method for using a sensor kit. Slide glass 26-1 is used as the first substrate. The slide glass 26-1 and the flat plane 25-3 of the second substrate 25-1 are silane-coated using 3-aminopropyltrimethoxysilane. Since the surface subjected to this processing is hydrophilic, an aqueous solution can be introduced into a cell made in the gap between the first substrate and the second substrate by capillarity. Moreover, a biochemical substance can be immobilized using an amino group introduced by this processing. Alternatively, like the first embodiment, a hydrophilic surface is obtained by silane-coating the surface of the substrate using 3-glycidoxypropyltrimethoxysilane, whereby, as well as by the use of an epoxy group introduced by this process, a biochemical substance can be immobilized.

Figure 26A:
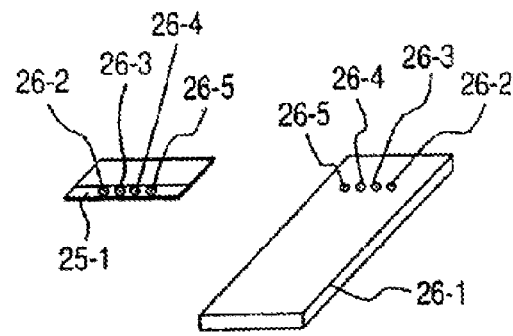
Figure 26B:
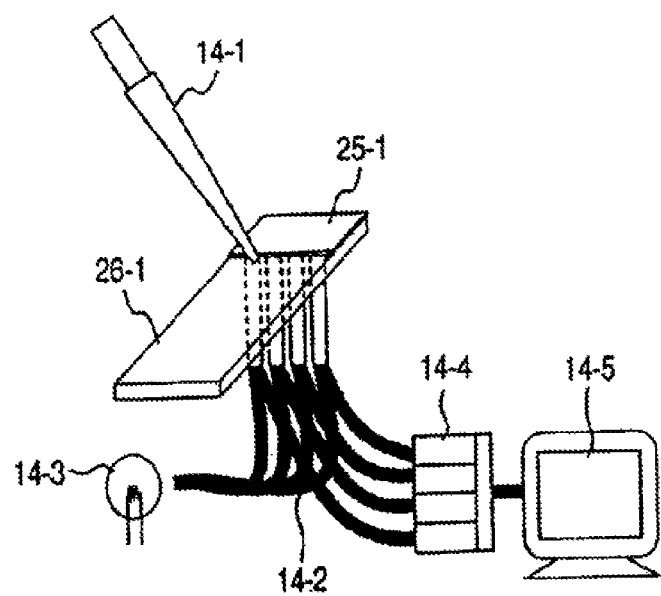

Subsequently, as shown in FIG. 26A, probes 26-2, 26-3, 26-4, and 26-5 are immobilized on the slide glass 26-1 and the flat plane 25-3 of the substrate 25-1. At this time, positions at which the probes are immobilized are so determined that the sites on which the same kind of probe is immobilized face each other when the substrates are faced each other. After the probe is immobilized, as shown in FIG. 26B, the planes on which the probes are immobilized are faced each other, and the substrates are fixed to each other with a cramp like the first embodiment. By this procedure, a gap with a vertical elevation 25-2 in the height direction is formed between the planes on which the probes are immobilized, respectively, and thus the cell can be formed.

It is possible to detect the binding of a target with the probe of this sensor kit by using the biochemical analyzer and the same measurement procedure as those of the first embodiment. At this time, since the second substrate 25-1 is opaque, the same effect as in the case where the second substrate in the first embodiment is specified to be an optical absorbing glass, such as of black color, that is, the transmitted light into the second substrate and indoor light can be prevented from affecting the measurement. Note that the example of forming the optical thin film of a refractive index of 2.2 was explained in this embodiment. However, the optical thin film may be formed on the first substrate instead.

What is claimed is:

1. A cell for biochemical analysis, comprising:
   a first member having a silicon substrate and an optical thin film on the silicon substrate, a first site of a surface of the optical thin film having a biochemical substance immobilized thereon; and
   a second member, a second site of a surface of the second member having the same biochemical substance as the biochemical substance immobilized on the first site of the surface of the optical thin film immobilized thereon;
   wherein the first site of the surface of the optical thin film and the second site of the surface of the second member face each other to form a gap for introducing an aqueous solution into the gap.

2. The cell for biochemical analysis according to claim 1, wherein same kind of linkers are on the surface of the optical thin film and the surface of the second member.

3. The cell for biochemical analysis according to claim 2, wherein the linkers are made of silane coupling agents.

4. The cell for biochemical analysis according to claim 1, wherein the optical thin film is a silicon nitride film.

* * * * *